United States Patent [19]

McNally et al.

[11] Patent Number: 4,833,073
[45] Date of Patent: May 23, 1989

[54] IMMUNOASSAY FOR TETRAHYDROCANNABINOL METABOLITES

[75] Inventors: Alan J. McNally, North Arlington; Alan Schwartz, Upper Montclair; Magdalena Usategui, Wayne, all of N.J.

[73] Assignee: Hoffmann-La Roche Inc., Nutley, N.J.

[21] Appl. No.: 7,838

[22] Filed: Jan. 27, 1987

[51] Int. Cl.$^4$ ............................................. G01N 33/53
[52] U.S. Cl. ..................................... 435/7; 435/28; 435/188; 436/518; 436/544; 436/545; 436/546; 436/547; 436/804; 436/805; 436/815; 549/390
[58] Field of Search ..................... 435/7, 28, 188; 436/518, 544, 545, 546, 547, 804, 805, 815, 901; 549/390

[56] References Cited

U.S. PATENT DOCUMENTS

| | | | |
|---|---|---|---|
| 3,649,650 | 3/1972 | Razdan et al. | 549/390 |
| 4,438,207 | 3/1984 | Fahrenholtz et al. | 436/543 |
| 4,650,771 | 3/1987 | Buckler et al. | 436/544 |
| 4,652,681 | 3/1987 | Eller et al. | 436/545 |

OTHER PUBLICATIONS

Yolken: Reviews of Infectious Diseases 4(1) pp. 35–45, 1982.
Childs et al., J. Anal. Toxicol. 8:220 (1984).
Fahrenholtz et al., J. Am. Chem. Soc. 89:5934 (1967).
Law et al., J. Anal. Toxicol. 8:14 (1984).
O'Connor et al., J. Anal. Toxicol. 5:168 (1981).
Razdan et al., J. Am. Chem. Soc. 96:5860 (1974).

Primary Examiner—Robert J. Warden
Assistant Examiner—Robert Benson
Attorney, Agent, or Firm—Jon S. Saxe; George M. Gould; Norman C. Dulak

[57] ABSTRACT

Novel cannabinol derivatives are provided which can be used in improved immunoassays for the detection in blood or urine samples of cannabinol metabolites.

8 Claims, 3 Drawing Sheets

IMMUNOASSAY FOR TETRAHYDROCANNABINOL METABOLITES

TECHNICAL FIELD

This invention relates to methods for the preparation of novel tetrahydrocannabinol derivatives and to the use of these derivatives as reagents in improved immunoassays for cannabinol metabolites in biological fluid samples.

BACKGROUND OF THE INVENTION

Increases in the use of marijuana have led to the development of assays for the detection of the primary active constituent of the plant, $\Delta^9$-tetrahydrocannabinol (THC), and, more particularly, metabolites of THC in urine and blood samples. These assays employ the use of labeled cannabinol derivatives in conjunction with antibodies against metabolites of the drug.

In practice, a blood or urine sample suspected to contain cannabinol metabolites (including glucuronides and other conjugation products) is contacted with the antibodies in the presence of a labeled derivative. To the extent that cannabinol metabolites are present in the sample, there will be competition for binding to the combining sites of the antibodies, and the amount of the labeled derivative bound will be reduced in proportion to the degree of such competition.

Descriptions of some representative immunoassays can be found in O'Connor et al., J. Anal. Toxicol. 5:168 (1981), Law et al., J. Anal. Toxicol. 8:14 (1984) and Childs et al., J. Anal. Toxicol. 8:220 (1984). In all of these references, it is the displacement of some of the labeled cannabinol derivative by metabolites in the assay samples that is the basis of the assays described. Superior assay results will be obtained when the labeled derivative is specifically recognized by the antibodies and yet easily displaced by the various products of cannabinol metabolism.

SUMMARY OF THE INVENTION

The present invention relates to novel compounds which are derivatives of cannabinol of the formulae

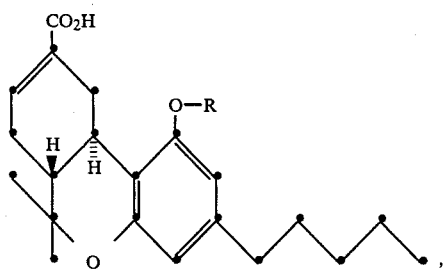

where R is an attachment chain selected from the group consisting of a p-aminobenzyl group or a branched or linear aminoalkyl group having from 1 to 7 carbon atoms or an organic or mineral acid addition salt thereof, an isocyanate or isothiocyanate derivative of the p-aminobenzyl or aminoalkyl group, a carboxyl terminated derivative of the aminoalkyl group having from 1 to 7 additional carbon atoms or a salt thereof, and an activated derivative of the carboxyl terminated derivative.

This invention further relates to the use of labeled derivatives of the above compounds with antibodies against cannabinol metabolites or derivatives for the detection of cannabinol metabolites in blood or urine samples. Detection of the metabolites is facilitated by the use of the labeled derivative compounds, which comprise the compounds of the invention covalently coupled to a suitable reporter molecule.

BRIEF DESCRIPTION OF THE FIGURES

The present invention may be more readily understood by reference to the following figures, in which.

DESCRIPTION OF THE INVENTION

Figure 1:
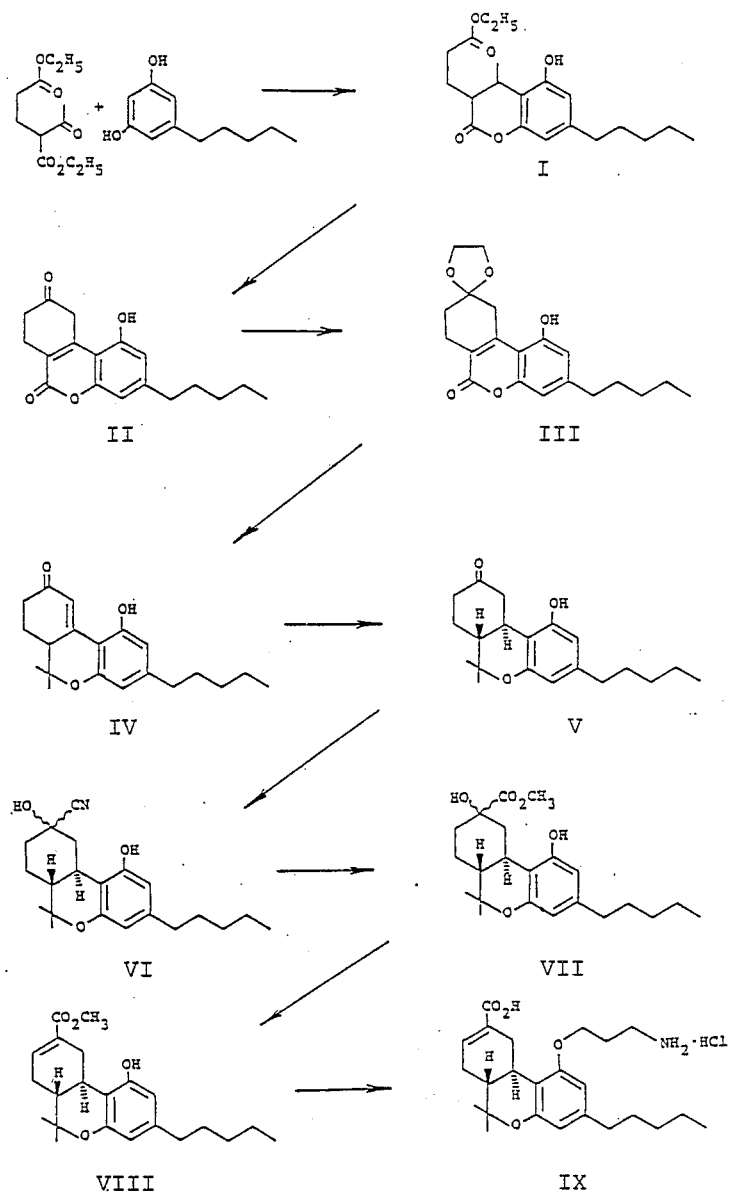
FIG. 1 shows the formulae of the starting materials and intermediates involved in the synthesis of (trans-rac)-1-(3-aminopropoxy)-6a,7,10,10a-tetrahydro-6,6-dimethyl-3-pentyl-6H-dibenzo(b,d)pyran-9-carboxylic acid monohydrochloride.

The immunoassays of the present invention are directed to the assay of cannabinol metabolites in biological fluids such as human blood and urine samples. As used herein, the term "cannabinol metabolites" means $\Delta^8$ or $\Delta^9$ tetrahydrocannabinol and the catabolic products of these compounds, including conjugation products such as the glucuronides. The term "cannabinol derivative" means a chemically synthesized derivative of $\Delta^8$ or $\Delta^9$ tetrahydrocannabinol.

Antibodies used in the invention can be prepared using any one of a wide range of possible immunogens. These immunogens comprise a cannabinol metabolite or derivative conjugated to a suitable immunogenic carrier molecule. Conjugation to a carrier is necessary because the cannabinol metabolites or derivatives themselves are haptens (molecules which are capable of specifically binding to an antibody but incapable of eliciting antibody production, i.e., they are not immunogenic).

As used herein, the term "immunogenic carrier molecule" means macromolecules which have the property of independently eliciting an immunological response in a host animal and which can be covalently coupled to the cannabinol metabolite or derivative. Suitable carrier molecules include, e.g., proteins; natural or synthetic polymeric compounds such as polypeptides; polysaccharides etc. Protein carrier molecules are especially preferred. Once coupled to a carrier molecule, the cannabinol metabolite or derivative becomes immunogenic due to what is commonly known as the "carrier effect".

Protein carriers which may be used in this invention include but are not limited to mammalian serum proteins such as keyhole limpet hemocyanin, human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the cannabinol metabolite or derivative are to be elicited.

Covalent coupling to the carrier molecule can be carried out by methods well known in the art, the exact choice of which will be dictated by the nature of the functional groups in the cannabinol metabolite or derivative and in the carrier molecule available for coupling.

Once prepared, the immunogen can be used to induce the formation of antibodies that are specific to cannabinol metabolites in host animals by injecting the immunogen in a host animal, preferably using a conventional adjuvant such as Freund's complete or incomplete adjuvant and the like. Suitable host animals include rabbits, horses, goats, guinea pigs, rats, cows, sheep, etc. The resulting antiserum must be such that the antibodies contained therein, called anti-THC antibodies, are capable of specifically binding to the cannabinol metabolites which are to be assayed and to the labeled compounds of the invention bearing reporter groups, as described below. The suitability of the antiserum product can be rapidly ascertained by routine experimentation.

In an illustrative embodiment, anti-THC antibodies produced against three different conjugates based upon three THC derivatives coupled at the 9 position were pooled for use in the invention (see Example 14). It again must be stressed, however, that the exact nature of the conjugates used to make the antibodies is not critical to the invention, as long as the resulting antibodies have the requisite broad specificity for THC metabolites.

Although whole antiserum can be used, the IgG fraction is preferably isolated by salt fractionation, such as ammonium sulphate precipitation, by DEAE chromatography or by other means known in the art.

Some of the novel cannabinol compounds of the present invention are derivatives of a major metabolite of THC,

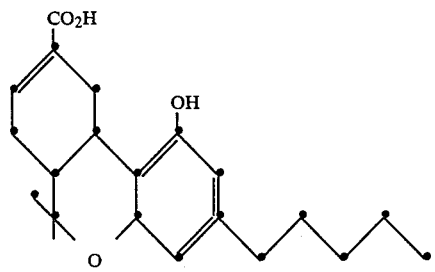

in which the phenolic hydroxyl group is modified by replacement of the phenolic hydrogen by a p-aminobenzyl group or an amino-terminal alkyl group which can have from 1 to 7 carbon atoms. Where an amino alkyl group is used, the group may be branched or straight chain, such as aminopropyl, aminoisopropyl, aminobutyl, aminoisobutyl and the like.

The amino compounds and intermediates of the invention may be utilized as free bases or as acid addition salts of organic or mineral acids. Representative addition salts that could be used include hydrochloride, hydrobromide, sulfonate, methanesulfonate, nitrate, phosphate, trifluoroacetate, oxalate, maleate, succinate, acetate and the like.

Other compounds of the invention are isocyanate or isothiocyanate derivatives of the amino compounds, which can be prepared by treating the p-aminobenzyl or amino-terminal alkyl groups with phosgene and thiophosgene, respectively.

Still other compounds of the invention are carboxyl terminated derivatives of the aminoalkyl compounds. Such carboxyl derivatives can be prepared by methods commonly used in the art. For example, the amino-terminal alkyl groups can be treated with chloro, bromo or iodo haloorganic acids having from 1 to about 7 carbon atoms, to produce carboxyl terminal derivatives. Such compounds can be employed as such or as salts such as $Na^+$, $NH_4+$ and the like. These carboxyl derivatives can be coupled to amino or hydroxyl groups on suitable reporter molecules through the use of coupling agents such as 1-ethyl-3-(3-dimethylaminopropyl) carbodiimide or, preferably, dicyclohexylcarbodiimide.

Alternatively, the carboxyl compounds can be further modified to produce activated derivatives such as N-hydroxysuccinimide ester derivatives. Such derivatives can be prepared by reacting the carboxyl derivatives with a desired activating compound such as N-hydroxysuccinimide in the presence of a coupling agent such as dicyclohexylcarbodiimide.

It must be stressed that it is the availability of an attachment chain at the phenolic hydroxyl group of THC that imparts superior diagnostic properties to the compounds of this invention. The skilled artisan will immediately recognize that through the use of the intermediates of the invention, there are many other ways that similar attachment chains with similar functional groups suitable for coupling to reporter groups can be prepared. For example, a carboxyl terminated derivative could be prepared directly without proceeding by way of an amino derivative as described herein.

The available functional groups in the compounds of the invention provide a convenient point for labeling by the covalent coupling of an appropriate reporter group, to facilitate detection in the immunoassays.

Suitable reporter groups for the labeled compounds include, e.g., biotin (to be use in conjunction with appropriately tagged avidin); fluorescent, chemiluminescent or bioluminescent groups; or radioisotopes such as $^3H$, $^{14}C$, $^{35}S$ and $^{125}I$, which can readily be introduced into the molecule in many forms well known in the art, due to the availability of the amino and carboxyl groups in the compounds. Such groups can be detected and quantified by liquid scintillation spectrometry, fluorescence spectroscopy, fluroescence polarization, etc. as appropriate.

Alternatively, conjugate compounds can be prepared in which the compounds of the invention are covalently linked to an enzyme by the free functional group, including but not limited to various peroxidases, glucose oxidase, β-galactosidase and alkaline phosphatase. Horseradish peroxidase, which can be detected by spectrophotometric analysis of its activity on a substrate such as pyrogallol or o-phenylenediamine, is especially preferred. Where enzymes are used, the conjugate compounds can be used in conjunction with conventional additives, buffers, diluents and enzyme stabilizers.

The cannabinol derivatives of this invention make superior reagents for use in immunoassay, in part because they provide functional groups at which labeling can be carried out. More, importantly, the presence of the phenolic oxygen side chains creates compounds that can still bind to anti-THC antibodies but which do so with reduced affinity. As a result, they are more easily displaced from the antibody combining sites by assay sample cannabinol metabolites. The immunoassays employing these labeled compounds are thus extremely sensitive.

The anti-THC antibodies and labeled compounds of the invention can be used in a variety of immunoassays for the detection of cannabinol metabolites. Such immunoassays could take the form of a radiommunoassay, either in free solution or solid state. Alternatively, enzyme immunoassays could be carried out, again either in free solution or solid state. Solid state assays can be carried out by the use of solid particles onto which the antibodies have been immobilized. Particles which could be coated with the antibodies include, e.g., latex beads, liposomes, erythrocytes, polyacrylamide beads, polystyrene beads or beads made of any of a number of other suitable polymers. The immunoassays can be direct or indirect, with the application of a second antibody directed against the anti-THC antibodies.

In a preferred embodiment of the invention, a sample suspected to contain cannabinol metabolites is mixed with known amounts of a labeled compound of the invention and known amounts of anti-THC antibodies absorbed onto a polystyrene bead. Following an incubation period, the bound labeled compound is separated from the free labeled compound, and the amount of either the free or bound compound is measured and compared to the values obtained by subjecting samples containing known amounts of a cannabinol metabolite to the same analytical steps.

EXAMPLES

Figure 2:
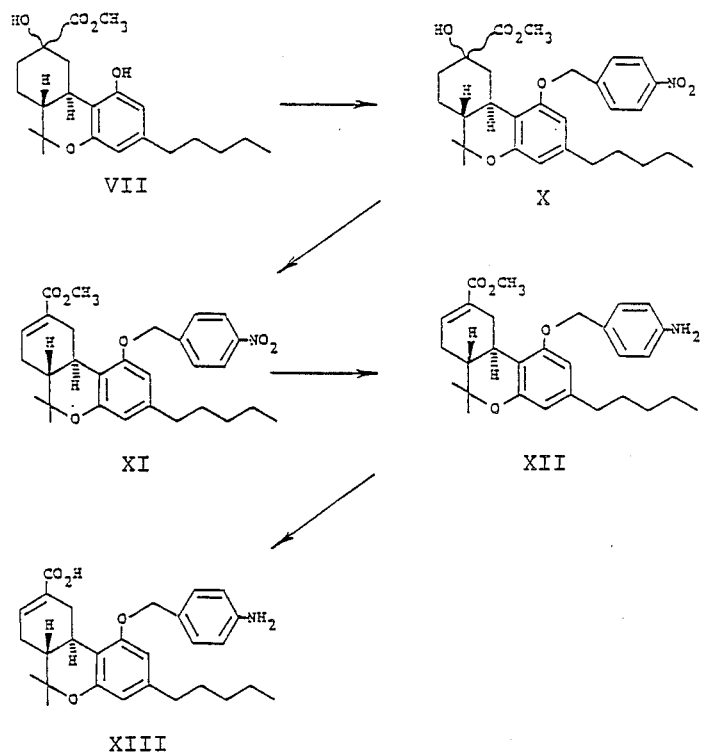
FIG. 2 shows the formulae of the intermediates and final product of the synthesis of (trans-rac)-6a,7,10,10a-tetrahydro-1-(4-aminobenzyl)-6,6-dimethyl-3-pentyl-6H-dibenzo(b,d)pyran-9-carboxylic acid.

The following are non-limiting examples which illustrate the synthesis of some of the novel cannabinol derivatives of the invention and the use of one of these compounds in an enzyme immunoassay system. The chemical structures of the intermediates and final product of the synthesis of (trans-rac)-1-(3-aminopropoxy)-6a,7,10,10a-tetrahydro-6,6-dimethyl-3-pentyl-6H-dibenzo-[b,d] pyran-9-carboxylic acid monohydrochloride are shown in FIG. 1. The chemical structures of the intermediates and final product of the synthesis of (trans-rac)-6a,7,10,10a-tetrahydro-1-(4-aminobenzyl)-6,6-dimethyl-3-pentyl-6H-dibenzo(b,d)pyran-9-carboxylic acid are shown in FIG. 2. The Roman numeral designations of the compounds in the headings of Examples 1–13 refer to the structural formulae shown in FIGS. 1 and 2.

EXAMPLE 1

Preparation of Ethyl 4-methyl-5-hydroxy-7-pentylcoumarin-3-propionate (I)

A 5-liter flask equipped with a mechanical stirrer, thermometer and nitrogen bubbler was charged with 210.0 g (1.17 moles) of olivetol (Aldrich), 300.0 g (1.30 moles) of diethyl-2-acetoglutarate (Aldrich) and 180.0 g (1.117 moles) of phosphorus oxychloride. The mixture was stirred at room temperature and slowly began to thicken. After three days, the mixture had solidified, at which time it was allowed to stand for an additional 7 days without stirring.

The solid mixture (light green in color) was dissolved in 2.0 l of methylene chloride and transferred to a 6-liter separatory funnel. The organic layer was washed with 10 l of deionized water in five equal portions and dried over anhydrous $Na_2SO_4$, and the solvent was then stripped off on a rotary evaporator (40° C., 50 mm Hg) to yield 672.7 g (166%) of a pink solid. This solid was redissolved in 1.0 l of ethyl acetate on a steam bath followed by the addition of hexanes with continued heating. The solution was allowed to cool to room temperature and then placed in a freezer (−10° C.) overnight. Resulting crystals were filtered on a Buchner funnel, washed with about 1.0 l of a mixture of cold hexanes:ethyl acetate (2:1), and dried at 100° C/10 mm Hg in a vacuum oven for 20 hours to yield 243.5 g (60%) of light pink crystals, m.p. 118–120° C.

EXAMPLE 2

Preparation of 7,10 Dihydro-1-hydroxy-3-pentyl-6H-dibenzo(b,d)pyran-6,9-(8H)-dione (II)

A 5-liter flask equipped with a mechanical stirrer, thermometer, addition funnel and nitrogen bubbler was charged with 80.0 g (2.0 moles) of 60% NaH dispersion in mineral oil (Aldrich). The mineral oil was removed by washing the dispersion with 1500 ml of hexanes (Fisher) in three equal portions. One hundred and sixty grams (0.462 mole) of compound I were added to the flask, and the two solids were mixed mechanically. A 20° C. constant temperature water bath was placed under the flask, and 1.4 l of distilled dimethylsulfoxide (DMSO) was carefully added dropwise so that the temperature of the mixture never rose above 20° C.

After 6 hours the addition was complete, and the bath was removed. The mixture was stirred for an additional hour and then placed in a freezer (−10° C.) overnight. The next day the mixture was warmed to room temperature and poured into an extractor filled with 12 l of ice water and 250 ml of concentrated HCl, when it was rapidly stirred for 2 hours. As the mixture was stirred, solids began to precipitate. These solids were collected by filtration through a Buchner funnel and washed with 200 ml of a saturated $NaHCO_3$ solution followed by 250 ml of deionized water. The solids were air dried and then dried in a vacuum over (100° C./1 mm Hg) for 16 hours to yield 124.8 g (90%) of an off-white solid, m.p. 181°–184° C.

EXAMPLE 3

Preparation of 7,8,9,10-Tetrahydro-1-hydroxy-3-pentylspiro-6-H-dibenzo(d,b)-pyran-9,2-(1'-3')-dioxolan-6-one (III)

A 3-liter flask equipped with a thermometer, mechanical stirrer, Dean-Strak trap, condenser and nitrogen bubbler was charged with 20.0 g (0.32 mole) of ethylene glycol, 18.4 g (0.062 mole) of compound II, 1.0 g of p-toluenesulfonic acid monohydrate and 1.0 l of toluene. The solution was refluxed overnight, and 16.3 ml of azeotropic water were collected in the trap. The reaction was cooled to room temperature and transferred to a 2-liter separatory funnel, where it was washed first with 300 ml of a saturated $NaHCO_3$ solution and then with 300 ml of deionized water.

The toluene layer was dried over $Na_2SO_4$ and then stripped on a rotary evaporator (60° C./50 mm Hg) to a brown oil that was redissolved in about 100 ml of methylene chloride. Twenty ml of hexanes were added to the solution, and the mixture was placed in a freezer (−10° C.) overnight. Crystals formed which were collected by filtration on a Buchner funnel, washed with 30 ml of hexanes and dried overnight in a vacuum oven (25° /1 mm Hg) to give 14.7 g (69%) of an off-white solid, m.p. 110°–113° C.

EXAMPLE 4

Preparation of dl-1-Hydroxy-3-pentyl-6,6-dimethyl-6a,7-dihydro-6H-dibenzo(d,b)pyran-9(8H)-one (IV)

A 3-liter flask equipped with a mechanical stirrer, thermometer, heating mantle, addition funnel, condenser and a nitrogen bubbler was charged with 12.5 g (0.515 mole) of Mg turnings (Fisher) and 500 ml of anhydrous ether. Then, 73.1 g (0.515 mole) of iodomethane (Aldrich) was added dropwise to the suspension at such a rate as to maintain a gentle reflux. After completion of the addition (about 30 minutes), the grey-black solution was refluxed for an additional hour, at which time a solution of 16.9 g (0.040 mole) of compound III in 300 ml of anhydrous tetrahydrofuran (THF) was added dropwise to the refluxing solution over a period of 20 minutes. The mixture rapidly turned yellow, and solids deposited on the sides of the flask.

The resulting heterogeneous mixture was refluxed overnight and then cooled to room temperature. The mixture was quenched by the careful addition of 56 ml of 1N HCl over about 20 minutes to produce a gently refluxing solution. An additional 210 ml of 6N HCl were added over 20 minutes, and the dark green mixture was stirred for an additional hour and transferred to a 2-liter separatory funnel, where the aqueous layer was discarded.

The ether layer was extracted in succession with 200 ml of deionized water, 200 ml of a saturated $NaHCO_3$ solution, and 200 ml of deionized water, after which the solution was dried over $Na_2SO_4$ and stripped on a rotary evaporator (40° C./50 mm Hg) to a dark green oil. Fifty ml of ether was added, and the mixture was allowed to stand overnight at room temperature. Crystals formed which were collected on a Buchner funnel, washed twice with 25-50 ml of cold ($-10°$ C.) ether:-hexanes (1:1) and dried overnight in a vacuum oven (25° C./1 mm Hg) to give 9.7 g (63%) of a light yellow material, m.p. 198°-200° C.

Concentration of the mother liquor on a rotary evaporator (40° C./50 mm Hg) and the addition of 10 ml of ether produced additional solids that were dried in a vacuum oven (25° C./1 mm Hg) to give 1.3 g of a light green solid, m.p. 193°-198° C. Overall yield was 71%.

EXAMPLE 5

Preparation of dl-6ab,7,10,10a-Tetrahydro-1-hydroxy-6,6-dimethyl-3-pentyl-6H-dibenzo(b,d)pyran-9(8H)-one (V)

A 2-liter jacketed resin flask equipped with a mechanical stirrer, dry-ice condenser, addition funnel and gas inlet valve was charged with 1.5 l of liquid $NH_3$, and 0.15 g of Li wire (Alfa) was added, which turned the solution blue. After 3 minutes, a solution of 32.0 g (0.102 mole) of compound IV in 500 ml of dry THF was added dropwise until the blue color faded. This process was repeated until a total of 2.7 g (0.39 g-atom) of Li wire had been added and the addition of compound IV was complete (about 2 hr). The blue solution was stirred for 15 minutes at $-33°$ C. and then quenched with 150 ml of saturated $NH_4Cl$, added carefully over a period of 10 minutes.

The $NH_3$ was allowed to evaporate rapidly (over about 2.5 hours), after which 500 ml of deionized water were added. The pH of the solution was adjusted from 12 to 1 with the careful addition (over about 2 hr) of 800 ml of concentrated HCl. The solution was extracted with 1.5 l of methylene chloride in three equal portions, and the organic phase was dried over $Na_2SO_4$ and stripped on a rotary evaporator (40° C./50 mm Hg) to a yellow, oily solid.

The solid was redissolved in about 100 ml of chloroform on a steam bath, and 500 ml of hexanes were added. The solution was concentrated in a rotary evaporator (35° C./50 mm Hg) until about 200 ml of distillate had been collected. Crystals began to form and the mixture was allowed to stand overnight at room temperature, after which the solids were collected by filtration on a Buchner funnel and washed with 1.5 l of warm (50° C.) hexanes in three equal portions.

The washed solids were dried overnight in a vacuum oven (25° C./1 mm Hg) to yield 27 g (84%) of an off-white solid, m.p. 161°-164° C. Thin layer chromatographic comparison with authentic standards in hexanes:EtOAc (3:1) showed that the solid material was primarily compound V, with some contaminating cis isomer. Purification of the material was carried out by one of two methods.

In the first purification method, a high pressure liquid chromatography (HPLC) Magnum 70 column packed with Partisil 40 silica and employing hexanes:EtOAc (4:1) as the mobile phase was used. A 15-20 g sample was injected into the column and 500 ml fractions were collected, with a total of 8.5 l of mobile phase applied. By this procedure, 72.1 g of the cis/trans mixture was separated into the pure components to yield 55.1 g (76%) of the trans compound V, m.p. 163°-165° C. and 10.3 g (14%) of the corresponding cis compound, m.p. 145°-148° C.

In an alternative procedure, isomerization was carried out to isomerize all of the mixture to the trans compound V. A 500ml flask equipped with a mechanical stirrer, thermometer and nitrogen bubbler was charged with 11.9 g (0.037 mole) of the above solid material, dissolved in 250 ml of methylene chloride and cooled to $-10°$ C. (ice-salt bath). The solution was charged with 17.3 g (0.129 mole) of $AlCl_3$, which raised the internal reaction temperature to $-5°$ C. The suspension was stirred at $-5°$ C. Δ 5° C. for 5 hours and then poured into about 500 ml of ice water and transferred to a separatory funnel, where the phases were allowed to separate.

The methylene chloride layer was dried over anhydrous $Na_2SO_4$, concentrated on a rotary evaporator (40° C./50 mm Hg) to an off-white solid, suspended in 500 ml of hexanes, and heated to reflux on a steam bath for 15 minutes. The warm suspension was filtered on a Buchner funnel, washed with about 100 ml of boiling hexanes, and dried in a vacuum oven (25° C./10 mm Hg) overnight to yield 9.5 g (80%) of white, solid compound V, m.p. 161°-166.5° C.

EXAMPLE 6

Preparation of (trans-rac)-6a,7,8,9,10,10a-Hexahydro-1,9-dihydroxy-6,6-dimethyl-3-pentyl-6H-dibenzo(b,d)pyran-9-carbonitrile (VI)

A solution of 5 g (0.0158 mole) of compound V in 175 ml of methanol was added to a suspension of 5 g (0.102 mole) of sodium cyanide in 20 ml of methanol, and the resulting mixture was stirred at room temperature under nitrogen for 2 hours. A solution of 5.75 ml of glacial acetic acid in 50 ml of methanol was added to the mixture, and stirring was continued for 30 minutes. The pH of the mixture was adjusted to about 2 with anhydrous HCl, and the mixture was stirred overnight under nitrogen.

The solvent was distilled off using a 40° C. water bath and aspirator over a 1-hour period, after which the residue was partitioned between 75 ml of water and 100 ml of methylene chloride. The aqueous layer was extracted with an additional 100 ml of methylene chloride, after which the combined organic layers were dried over anhydrous Na$_2$SO$_4$ and evaporated in a rotary evaporator (40° C./20 mm Hg) to dryness. Further drying was carried out for 0.5 hr at 0.5 mm Hg, to yield 5.5 g (100%) of compound VI as a light yellow foam. This material was used without further purification for the preparation of compound VII, although an analytical sample was recrystallized from methylene chloride/petroleum ether (1:10) to produce colorless needles, m.p. 131°–133° C.

EXAMPLE 7

Preparation of
(trans-rac)-6a,7,8,9,10,10a-Hexahydro-1,9-dihydroxy-6,6-dimethyl-3-pentyl-6H-dibenzo(b,d)pyran-9-carboxylic Acid Methyl Ester (VII)

A stirred solution of 5.5 g (0.0160 mole) of compound VI in 150 ml of methanol was treated by bubbling in anhydrous HCl at 3° C. in an ice bath over a period of 1.25 hours to saturation. The flask was capped with a septum and kept at −20° C. for 48 hours, after which 75 ml of 6N aqueous HCl were added. The mixture was evaporated in a rotary evaporator (35° C./20 mm Hg) and then at 0.5 mm Hg to produce an oil.

The oil was suspended in 150 ml of 50% aqueous methanol and allowed to stand overnight at 25° C. A copious white precipitate formed which was collected by filtration and then dissolved in 250 ml of ethyl acetate. A small amount of water was separated from the mixture, and the organic layer was dried over anhydrous Na$_2$SO$_4$ and then evaporated in vacuo (30° C./20 mm Hg) to dryness.

The residue was triturated with 50 ml of petroleum ether (bp 30°–60° C.) The solids were collected by filtration, washed with 50 ml of petroleum ether in two equal portions, and dried in vacuo (40° C., 0.5 mm Hg) for 2 hours to yield 3.1 g (53%) of a colorless solid, m.p. 178°–180° C. The mother liquors were evaporated to yield 1.3 g (22.5%) of a yellow oil which NMR analysis showed to be the epimeric hydroxy ester of compound VII. The total yield was thus 75%.

EXAMPLE 8

Preparation of
(trans-rac)-6a,7,10,10a-Tetrahydro-1-hydroxy-6,6-dimethyl-3-pentyl-6H-dibenzo(b,d)pyran-9-carboxylic Acid Methyl Ester (VIII)

A 50-ml reaction flask equipped with a nitrogen bubbler and a magnetic stirrer was charged with 1.4 g (0.0037 mole) of compound VII, 10 ml of pyridine and 2.0 ml of thionyl chloride and then stirred at room temperature under nitrogen for 1 hour. The mixture was quenched by pouring into 30 ml of ice water and then extracted into 90 ml of ethyl acetate in three equal portions.

The organic layer was dried over anhydrous Na$_2$SO$_4$ and evaporated to dryness in vacuo (25° C., 1 mm Hg) to yield 1.2 g of a solidified foam. This foam was triturated with 30 ml of petroleum ether (30°–60° C.) to give 975 mg (73%) of a light yellow solid, m.p. 107°–110° C. An analytical sample was recrystallized from ether-hexanes (1:6) to give colorless crystals, m.p. 139°–141° C.

EXAMPLE 9

Preparation of
(trans-rac)-1-(3-Aminopropoxy)-6a,7,10,10a-tetrahydro-6,6-dimethyl-3-pentyl-6H-dibenzo(b,d)pyran-9-carboxylic Acid Monohydrochloride (IX)

Three hundred and fifty eight mg (0.001 mole) of compound VIII were added to a suspension of 60 mg (0.0015 mole) of sodium hydride (Aldrich, 60% in mineral oil, prewashed with hexane) in 3.0 ml of N,N-dimethylformamide (DMF), and the mixture was stirred at room temperature under nitrogen for 30 minutes. Then, 560 mg (0.00021 mole) of N-3-bromopropylphthalimide were added to produce a brown solution which was stirred under nitrogen for 3 hours.

The mixture was poured into 20 ml of ice water and extracted into 40 ml of ethyl acetate in two equal portions. The organic layers were dried over anhydrous Na$_2$SO$_4$ and evaporated in vacuo (25° C., 1 mm Hg) to yield 740 mg of a yellow oil. The oil was dissolved in 10 ml of hexanes:ethyl acetate (7:3) and purified by column chromatography in a 28 g silica gel column which had been prepacked in hexanes:ethyl acetate (7:3). 200 ml fractions were collected, and those containing the desired product as shown by TLC on silica gel were evaporated in vacuo (25° C., 1 mm Hg) to give 322 mg (57.9%) of a colorless foam.

All of the foam was dissolved in 10 ml of 15% methylamine in methanol, stirred under nitrogen at room temperature for 1 hour and then evaporated in vacuo (25° C., 1 mm Hg) to dryness. The residue was taken up in a mixture of 10 ml of 2N NaOH and 10 ml of methanol and stirred under nitrogen overnight. The mixture was then evaporated in vacuo (25° C., 50 mm Hg) to near dryness, acidified with 6N HCl to pH 2, and extracted into 20 ml of ethyl acetate in two equal portions. The organic layers were dried over anhydrous Na$_2$SO$_4$ and evaporated to dryness in vacuo (25° C., 1 mm Hg), and the residue was triturated with ether to yield 90 mg (35%) of a colorless solid, m.p. 255°–257° C.

EXAMPLE 10

Preparation of
(trans-rac)-9-Hydroxy-6a,7,8,9,10,10a-hexahydro-1-(4-nitrobenzyl)-6,6-dimethyl-3-pentyl-6H-dibenzo(b,d)pyran-9-carboxylic Acid Methyl Ester (X)

A solution of 3.80 g (0.01 mole) of compound VII (see Example 8) in 150 ml of acetone was stirred under argon in a 500 ml three-neck flask, while 2.25 g (0.01 mole) of p-nitrobenzylbromide were added. Seven grams (0.05 mole) of finely pulverized anhydrous K$_2$CO$_3$ were added, and the resulting suspension was stirred rapidly under argon for 18 hours at 25° C. Analysis by thin layer chromatography (TLC) on silica gel plates in hexanes-ethyl acetate (7:3) with 10% CeSO$_4$/H$_2$SO$_4$, in which the results were visualized by a 10% phosphomolybdic acid/ethanol spray followed by heating, showed that the reaction was complete.

The mixture was filtered, and the residue was evaporated in vacuo to afford a yellow oil. This oil was dissolved in 5 ml of ether and poured over a 30 g plug of silica gel (70–230 mesh, E. Merck) in a sintered glass funnel. The plug was then eluted with 400 ml of ether, and the solvent was collected and evaporated to dryness on a rotary evaporator at 30° C.

Crystallization of the residue from ether-hexane (1:5) afforded 4.7 g of a fluffy white solid, m.p. 120°–123° C.

EXAMPLE 11

Preparation of (trans-rac)-6a,7,10,10a-Tetrahydro-1-(4-nitrobutyl-6,6-dimethyl-3-pentyl-6H-dibenzo(b,d)pyran-9-carboxylic Acid Methyl Ester (XI)

A mixture containing 2.5 g (0.00488 mole) of compound X, 15 ml of pyridine and 7.75 g (0.05075 mole) of $POCl_3$ was stirred at room temperature argon for 2 hours. The mixture was then poured into 100 ml of crushed ice and extracted with two 100-ml volumes of $CH_2Cl_2$. The organic layer was dried over $Na_2SO_4$, filtered and evaporated to dryness. The residue was taken up in 30 ml of $CH_2Cl_2$ and filtered through a plug of 20 g of silica gel (70–230 mesh). The plug was eluted with 100 ml of 1:1 hexane-ether, and the eluant was evaporated to dryness on a rotary evaporator at 30° C.

The residue, on trituration from 50 ml of petroleum ether, afforded in two crops 1.65 g (68%) of colorless prisms, m.p. 165°–167° C.

EXAMPLE 12

Preparation of (trans-rac)-6a,7,10,10a-Tetrahydro-1-(4-aminobenzyl)-6,6-dimethyl-3-pentyl-6H-dibenzo(b,d)pyran-9-carboxylic Acid Methyl Ester (XII)

A mixture containing 1.65 g (0.003 mole) of compound XI, 50 ml of $CH_2Cl_2$, 100 ml of ethanol and 3.4 g of 85% hydrazine hydrate (Aldrich) was rapidly stirred as a slurry. Five hundred milligrams of technical grade Raney Nickel (pre-rinsed with three 5-ml volumes of ethanol) in ethanol were then added in one portion. The mixture was rapidly stirred at room temperature for .1 hour, after which the catalyst was removed by filtration over a pad of Celite. The pad was rinsed with three 25-ml volumes each of $CH_2Cl_2$ and ethanol, and the combined filtrates were evaporated on a rotary evaporator (40° C., 5 mm Hg).

The residue was taken up in 25 ml of $CH_2Cl_2$, passed through a plug of 25 g of silica gel (70–230 mesh, E. Merck), and eluted with 300 ml of hexane-ethyl acetate (1:1). The combined eluant was evaporated on a rotary evaporator (40° C., 5 mm Hg) to afford 1.5 g of a yellow semi-solid. This crude product was repurified as described above and then crystallized from hexane-ether. A yield of 956 mg (62%) of a light yellow solid, m.p. 112°–114° C., was obtained.

EXAMPLE 13

Preparation of (trans-rac)-6a,7,10,10a-Tetrahydro-1-(4-aminobenzyl)-6,6-dimethyl-3-pentyl-6H-dibenzo(b,d)-pyran-9-carboxylic Acid (XIII)

A mixture containing 110 mg (0.22 mmole) of compound XII, 10 ml of 2N NaOH and 25 ml of ethanol was heated at reflux under argon for 1 hour. This mixture was evaporated on a rotary evaporator (30° C., 0.5 mm Hg) to remove most of the ethanol, bringing the volume to about 15 ml. The pH was adjusted to 2 with 6N HCl, and the mixture was extracted with two 30-ml volumes of $CH_2Cl_2$.

The organic layer was dried over $Na_2SO_4$ and then evaporated (30° C., 10 mm Hg) to yield 105 mg of a brown foam. The amorphous amino acid could not be crystallized, but analyses by 400 $MH_z$ NMR, IR and mass spectroscopy were consistent with the expected structure and showed that the product was essentially homogeneous.

EXAMPLE 14

Preparation of Anti-THC Antiserum

One hundred mg of a cannabinol derivative having the formula

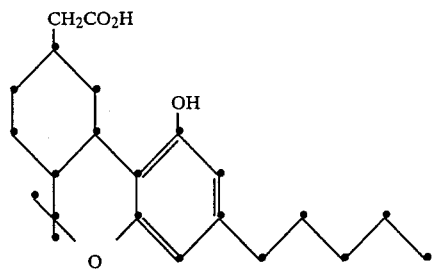

were dissolved in 20 ml of 30% methanol at pH 4.5. To this solution, 84 mg of 1-(3-dimethylaminopropyl)-3-ethylcarbodiimide hydrochloride were added and the pH was adjusted to 4.5. After mixing at room temperature for 30 minutes, 100 mg of methylated bovine serum albumin were added in 20 ml of water with mixing, and the pH was again adjusted to 4.5. The solution was mixed for 1 hour at room temperature and then overnight at 4° C., after which any unconjugated cannabinol derivative was removed by dialysis against 1000-ml volume changes of sodium phosphate buffer at 4° C., to produce a THC-methylated albumin conjugate.

One hundred mg of lipopolysaccharide (LPS; microbial source) in 5 ml of water were combined with 1 ml of 1.0M $NaIO_4$ and treated for 2 hours at room temperature in the dark. One ml of ethylene glycol was added, and the mixture was stirred for an additional 30 minutes at room temperature. The activated lipopolysaccharide was applied to a Sephadex ® G-25 column equilibrated with water, and a turbid effluent fraction was collected.

Five ml of tetrahydrofuran containing 38.75 mg of a cannibinol derivative having the formula

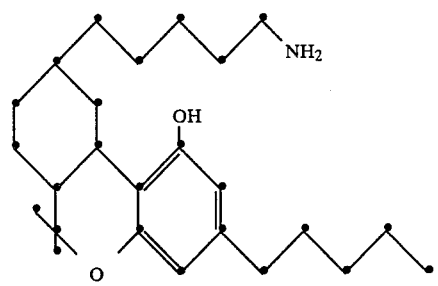

were added to the activated-LPS effluent, and the mixture was incubated for 18 hours at 22° C. in the dark. Two ml of a solution of 4.5 mg/ml $NaBH_4$ in $H_2O$ were added, and the mixture was incubated for 30 minutes at room temperature. Unconjugated THC derivative was removed by dialysis for 2 days against frequent changes of water and for 2 days against 0.1M acetic acid, pH 3.5, to yield a THC-LPS conjugate.

One hundred mg of human IgG were dissolved in 7 ml of 0.2M $NaHCO_3$, pH 9.6, and 108 mg of a cannabinol derivative having the formula

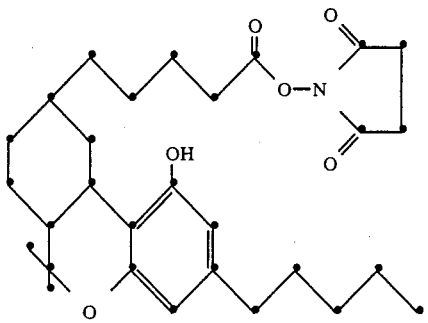

in 2 ml of dioxane were added. Nine additional ml of dioxane were added, and the mixture was mixed intermittently for 4 hours at 4° C., after which 180 ml of cold acetone were added. The mixture was centrifuged for 10 minutes at 2,000×g, and the pellet was washed once with 20 ml of cold acetone. Following centrifugation for 10 minutes at 2,000×g, the pellet was resuspended in 10 ml of phosphate buffered saline (PBS). Dialysis was carried out for 3 days at 4° C. against 2 changes per day of 1000-ml volumes of PBS, to produce a THC-human IgG conjugate.

New Zealand white rabbits were injected intramuscularly at the four axillary regions with 200 μg of THC in the form of one of the above conjugates in 1 ml of Freund's complete adjuvant. Booster injections containing 100 μg of the same conjugates were given after 2 weeks in 1 ml of Freund's incomplete adjuvant, and antiserum was harvested from the ear veins after 4 weeks.

Acceptable anti-THC antisera from the three rabbits were pooled for use as described below.

EXAMPLE 15

Purification of Anti-THC IgG

Ten milliters of a saturated ammonium sulfate solution were slowly added dropwise to 20 ml of anti-THC antiserum, with continual stirring at 23° C. Initially, a white precipitate formed which was allowed to redissolve prior to further ammonium sulfate addition. After about 6 ml of the ammonium sulfate solution had been added, the precipitate persisted, and from that point, the slow dropwise addition has continued without pause. Stirring of the suspension was continued for 2 hours at room temperature, after the last of the ammonium sulfate solution had been added, after which the mixture was centrifuged at 1,500×g for 30 minutes at room temperature. This procedure puts most of the IgG in the pellet.

After centrifugation, the supernatant fluid was decanted, and the pellet was dissolved by the addition of TRIS/saline (composition) to a final volume of 20 ml. The IgG in the solution was reprecipitated by repetition of the above ammonium sulfate addition and centrifugation steps, after which the supernatant fluid was again decanted. The pellet was dissolved in 10 ml of 0.02M Tris/saline, pH 7.5, with 0.01% thimerosal (sodium ethylmercurithiosalicylate).

To remove the ammonium sulfate from the IgG-containing solution, dialysis was carried out overnight at 4° C. against three 2-liter volumes of 0.02M Tris/saline. The material in the dialysis bag was then brought to a final volume of 20 ml by the addition of 0.02M Tris/saline. This solution was centrifuged at 2,000×g for 30 minutes at 4° C., and a small pellet which was formed was discarded. Protein concentration in the final IgG-containing solution was then determined by spectrophotometric analysis at 280 nm to be about 5.3 mg/ml.

EXAMPLE 16

Preparation of Anti-THC Beads

A 4-liter vacuum flask was filled to the 2,500 ml mark with ¼" frosted polystyrene beads (Clifton Plastics, Inc., Clifton Heights, PA), and 2,500 ml of 95% ethanol were added with stirring. The flask was placed under vacuum (1 mm Hg) for 30 minutes at room temperature, and the ethanol was decanted. The ethanol addition, vacuum treatment and decanting steps were repeated twice more, after which the beads were suspended in 3 l of deionized water. The water was decanted, and the beads were twice more washed in this fashion with 3-liter portions of deionized water. Two liters of deionized water were then added to the decanted beads, and the mixture was allowed to stand overnight at room temperature. Throughout the washing procedure, it is important that the beads are never allowed to dry out.

To coat the washed beads with antibodies against THC, the anti-THC IgG solution described above was diluted to a final protein concentration of 25 μg/ml with 50 mM sodium borate buffer, pH 8.0 (coating solution). The beads were coated by adding 143 ml (enough to cover the beads) of the coating solution to a measured volume of 250 ml of the settled beads (about 1,000 beads) from which the water had been decanted, and then letting the mixture stand for 18–24 hours at 18°–26° C.

Following the coating procedure, the coating solution was decanted and discarded, and the beads were washed three times at 4° C. with 500 ml volumes of a washing buffer containing 0.01M sodium phosphate in 0.15M saline with 0.01% thimerosal, pH 7.2. Each time, the beads were thoroughly suspended in the washing solution by stirring, and the solution was decanted after the beads had been allowed to settle. Throughout this procedure, care was taken to ensure that the beads did not dry out.

Next, the beads were treated to block unsaturated sites, using one of two procedures. Throughout the procedures that follow, the beads were handled only with plastic or glass utensils.

A 250 ml settled volume (about 1,000 beads) of the washed anti-THC coated beads above was treated after decanting with about 143 ml (enough to cover the beads) of a 45° C. blocking buffer containing 100 mM sodium phosphate with 1.0% bovine serum albumin (BSA) and 0.05% thimerosal, pH 6.8, for 18–24 hours. Following the blocking buffer treatment, the beads were washed three times with 500 ml portions of fresh blocking buffer at 4° C. Each time, the beads were suspended in the buffer with stirring and then allowed to settle, and the buffer was decanted. For storage, a quantity of the blocking buffer sufficient to cover the beads was added, and the beads were kept at 4° C. until needed.

Of course, the above procedures can be scaled up as desired, as long as the relative proportions of beads and solutions were maintained.

EXAMPLE 17

Preparation of THC Derivative-Peroxidase Conjugates

Ten milligrams of horseradish peroxidase [Boehringer Mannheim or Seravac (Pel Freeze)] were activated for conjugation by dissolving in 3 ml of deionized water, stirring for 1 hour in the dark room at room temperature. One half ml of 0.1M sodium metaperiodate (sodium periodate) was slowly added to the above solution over 20 minutes with stirring in the dark room at room temperature. The sodium periodate solution was prepared fresh immediately before use, and the activation reaction was stopped by adding 0.5 ml of 0.5M ethylene glycol, chilled to 4°-8° C.

The mixture was immediately placed in dialysis tubing (Spectrapor, molecular weight cutoff 12,000–14,000) and dialyzed overnight at 4° C. against three 1-liter changes of 0.01M sodium acetate buffer, pH 5.5. Following dialysis, the material in the bag (volume 4.0 ml) was placed in a 10 ml amber Wheaton vial.

For the conjugation reaction, 4 ml of a 1:1 mixture of ethanol:0.4M sodium acetate buffer, pH 5.5 containing about 0.56 mg of (trans-rac)-1-(3-aminopropoxy)-6a,7,10,10a-tetrahydro-6,6-dimethyl-3-pentyl-6H-dibenzo (b,d) pyran-9-carboxylic acid monohydrochloride (compound IX, see FIG. 1 and Example 9, supra) were added dropwise with stirring to the activated peroxidase solution and allowed to react for 2 hours at room temperature in the dark.

To stabilize the Schiff's bases that had formed, 1 ml of 0.1M sodium cyanoborohydride was added to the peroxidase conjugation mixture, and the mixture was stirred for 2 hours at room temperature in the dark.

The stabilized conjugation reaction mixture was then divided into four equal portions and applied to four Pharmacia PD-10 columns which had previously been equilibrated with buffer containing 0.2M sodium phosphate, pH 6.8 (chromatography buffer). The applied portions were run into the tops of the column beds and overlaid with 4 ml of the chromatography buffer.

A volume of column eluate of about 12.4 ml was collected from each column. Spectrophotometric analysis at 403 nm showed that the recovery of peroxidase in conjugated form was about 66%, taking the extinction coefficient to be 2.3.

Five milliliters of the conjugate eluant solution were diluted with 0.2M sodium phosphate buffer, pH 6.8 (diluted THC-peroxidase conjugate reagent), for use as described below.

EXAMPLE 18

THC-Enzyme Immunoassay Protocol

A series of 11×75 mm polystryene test tubes was set up containing duplicate 50 ul aliquots of urine specimens to be analyzed or normal control or THC standard-containing urine samples. The standard and normal control aliquots were taken from normal urine samples containing 0, 50, 100, 200 or 500 ng/ml added 9-carboxy-11nor-$\Delta^9$-tetrahydrocannabinol (100 μg/ml in absolute ethanol, Research Triangle Institute, Research Triangle Park, NC). Two-hundred-fifty microliters of the diluted THC-peroxidase conjugate reagent were added to each tube, and the tubes were shaken. One anti-THC bead was then added to each tube, the contents of the tubes were mixed and the tubes were incubated for 30 minutes at room temperature.

After the incubation, the beads were washed three times by adding 3 ml aliquots of deionized water with shaking and then aspirating the water. Two-hundred-fifty microliters of a chromogen reagent containing 7.2 mg/ml o-phenylenediamine dihydrochloride and 6 mM $H_2O_2$ in 0.1M potassium citrate buffer, pH 5.25, with 0.1 ml/liter of solution Kathon CG ® (an isothiazolin solution from Rohm and Haas) added as a preservative to each washed bead, and the tubes were incubated for 10 minutes at room temperature in the dark. The reactions were then stopped by the addition of 1 ml of 1N sulfuric acid to each tube, and the absorbance of the sample solutions was measured at 492 nm.

Figure 3:
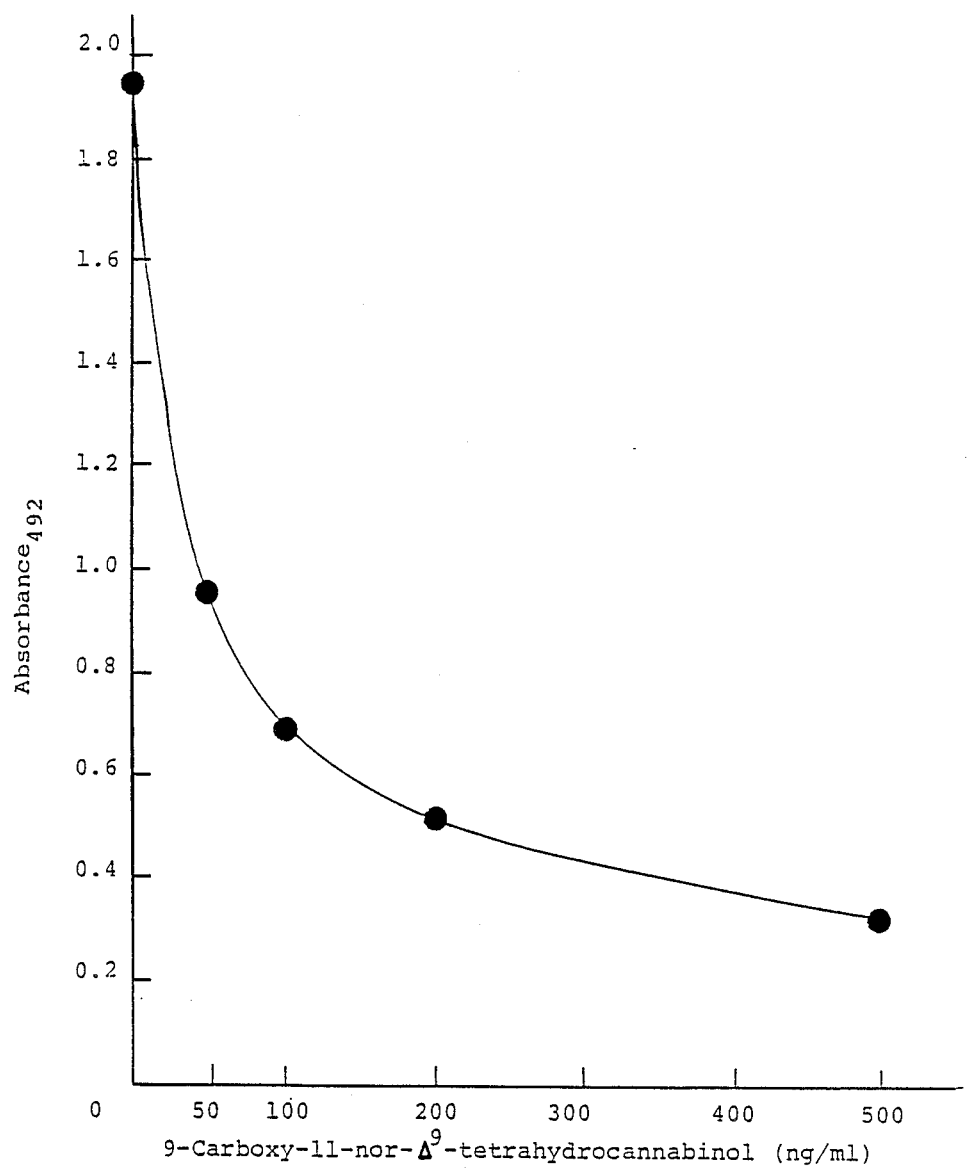
FIG. 3 is a graphical representation of a standard curve for the immunoassay of THC, showing change in absorbance at 492 nm as a function of 9-carboxy-11-nor-$\Delta^9$-tetrahydro-cannabinol concentration.

A plot of absorbance at 492 nm versus 9-carboxy-11-nor-$\Delta^9$-tetrahydrocannabinol concentration for the standards employed is shown in FIG. 3.

EXAMPLE 19

Clinical Sample Analysis

To establish the sensitivity and accuracy of the THC-enzyme immunoassay of the invention, a series of 60 clinical urine samples was evaluated using the assay (EIA) and the Roche THC radioimmunoassay (RIA) system, with the results shown in Table 1.

TABLE 1

Comparison of EIA and RIA THC Analyses

| Sample No. | THC (ng/ml) by EIA[a] | THC (ng/ml) by RIA[b] | Sample No. | THC (ng/ml) by EIA[a] | THC (ng/ml) by RIA[b] |
|---|---|---|---|---|---|
| 1 | 300 | >200 | 31 | >500 | >200 |
| 2 | >500 | >200 | 32 | >500 | >200 |
| 3 | >500 | >200 | 33 | >500 | >200 |
| 4 | 217 | >200 | 34 | 300 | >200 |
| 5 | 3.5 | 0.0 | 35 | >500 | >200 |
| 6 | >500 | >200 | 36 | >500 | >200 |
| 7 | >500 | >200 | 37 | 7.0 | 0.0 |
| 8 | >500 | >200 | 38 | >500 | >200 |
| 9 | >500 | >200 | 39 | 190 | 200 |
| 10 | 120 | 125 | 40 | 250 | >200 |
| 11 | 5.0 | 0.0 | 41 | 10.0 | 0.0 |
| 12 | 94 | 141 | 42 | 467 | >200 |
| 13 | 189 | >200 | 43 | 194 | 106 |
| 14 | 47 | 50 | 44 | 465 | >200 |
| 15 | 500 | >200 | 45 | 16.5 | 0.0 |
| 16 | 154 | >200 | 46 | >500 | >200 |
| 17 | 217 | 190 | 47 | >500 | >200 |
| 18 | 110 | 86 | 48 | >500 | >200 |
| 19 | 180 | >200 | 49 | 338 | 176 |
| 20 | 500 | >200 | 50 | >500 | >200 |
| 21 | >500 | >200 | 51 | 500 | >200 |
| 22 | 90 | 157 | 52 | 16.5 | 0.0 |
| 23 | 427 | >200 | 53 | 17.0 | 0.0 |
| 24 | 13 | 0.0 | 54 | >500 | >200 |
| 25 | >500 | >200 | 55 | 193 | 195 |
| 26 | >500 | >200 | 56 | 467 | 198 |
| 27 | >500 | >200 | 57 | 340 | 158 |
| 28 | 466 | >200 | 58 | >500 | >200 |
| 29 | 335 | >200 | 59 | >500 | >200 |
| 30 | 8.0 | 0.0 | 60 | 13.5 | 0.0 |

[a]EIA represents the THC-enzyme immunoassay of the invention.
[b]RIA represents the commercial THC radioimmunoassay system of Roche Diagnostic Systems, a division of Hoffmann-La Roche Inc., Nutley, New Jersey.

The threshold for a positive test in Table 1 was taken to be 50 ng/ml 9-carboxy-11-nor-$\Delta^9$-tetrahydrocannabinol in the EIA, and 100 ng/ml in the RIA. Based upon these criteria for a positive test, only sample 18 showed a discrepancy between the results obtained from the two analytical methods. This sample was positive by EIA but negative by RIA. Sample 18 was retested by both methods and found to be positive in the retests by both RIA and EIA.

As a further check on the specificity of the THC-enzyme immunoassay, a number of drugs not related to the cannabinoids were added to pooled normal human urine samples at a concentration of 10,000 ng/ml and tested by the method. None of these compounds, which are listed in Table 2, were positive in the assay.

TABLE 2

Drugs Tested for Cross-Reactivity

| | |
|---|---|
| Acetaminophen | Guaiacol glycerol ether |
| Acetylsalicyclic acid | Hydrochlorothiazide |
| Aminopyrine | Hydrocodone bitartrate |
| Amitryptyline | Hydromorphone hydrochloride |
| Amobarbital | p-Hydroxyphenobarbital monohydrate |
| Amphetamine | Imipramine |
| Ampicillin | Lidocaine |
| Apomorphine | Melanin |
| Ascorbic acid | Meperidine |
| Atropine | Methadone |
| Benzocaine | d-Methamphetamine hydrochloride |
| Benzoylecgonine (cocaine metabolite) | Methaqualone |
| Butabarbital | Methyprylon |
| Caffeine | Morphine |
| Calcium hypochlorite | Naproxen |
| Chlordiazepoxide | Niacinamide |
| Chloropheniramine | Norethindrone |
| Chloroquine | Oxazepam |
| Chlorpromazine | Oxycodone hydrochloride |
| Cocaine hydrochloride | Penicillin G |
| Codeine | Pentobarbital |
| Cyclopentobarbital | Phencyclidine |
| Dextromethorphan | Phenobarbital |
| Dextropropoxyphene HCl | Phenothiazine |
| Diallylbarbituric acid | Phenylbutazone |
| Diazepam | Phenylpronanolamine |
| Dihydrocodeine bitartrate | Procaine hydrochloride |
| 5,6 Dihydroxyindole | Promethazine |
| Diphenylhydantoin | Propoxyphene |
| Ecgonine hydrochloride | Quinine hydrochloride |
| Epinephrine | Sodium secobarbital |
| Erythromycin | Tetracycline |
| Estriol | Tetrahydrozoline |
| Gentisic acid | Trifluoperazine |
| Gluthethimide | Zomepirac |

Many modifications and variations of this invention may be made without departing from its spirit and scope, as will become apparent to those skilled in the art. The specific embodiments described herein are offered by way of example only, and the invention is limited only by the terms of the appended claims.

What is claimed is:

1. A method for the immunoassay of cannabinol metabolites, comprising:
   (a) mixing a sample suspected to contain cannabinol metabolites with known amounts of a labeled compound comprising a compound of the formula

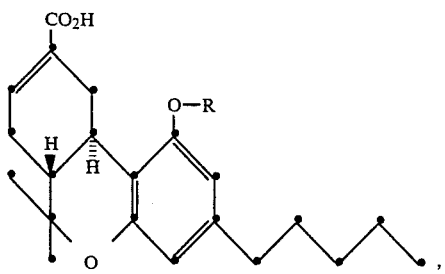

where R is an attachment chain selected from the group consisting of a p-aminobenzyl group or an organic or mineral acid addition salt thereof, a p-isocyanatobenzyl group, a p-isothiocyanatobenzyl group, a branched or linear aminoalkyl group having from 1 to 7 carbon atoms or an organic or mineral acid addition salt thereof, a branched or linear isocyanatoalkyl group having from 1 to 7 carbon atoms, a branched or linear isothiocyanatoalkyl group having from 1 to 7 carbon atoms, and a carboxyl-terminated derivative of the amino group in such aminoalkyl group, having from 1 to 7 additional carbon atoms, or an organic or mineral acid addition salt thereof; which group or derivative is covalently coupled to a reporter group; and antibodies prepared against a cannabinol metabolite conjugated at the 9 position to an immunogenic carrier, which antibodies are also capable of selectively binding the labeled compound;
   (b) separating the bound from the free labeled compound;
   (c) measuring the amount of either the free or the bound labeled compound;
   (d) comparing the amount of the labeled compound measured to values obtained from samples containing known amounts of a cannabinol metabolite; and
   (e) determining the amount of cannabinol metabolites in the sample from the comparison of step (d).

2. The method of claim 1 in which the antibodies are immobilized on a solid support.

3. The method of claim 1 in which the reporter group is an enzyme.

4. The method of claim 3 in which the enzyme is a peroxidase.

5. A method for the immunoassay of cannabinol metabolites, comprising:
   (a) mixing a sample suspected to contain cannabinol metabolites with known amounts of a labeled compound comprising (trans-rac)-1-(3-aminopropoxy)-6a, 7, 10, 10a-tetrahydro-6,6-dimethyl-3-pentyl-6H-dibenzo(b,d)pyran-9-carboxylic acid or an organic or mineral acid addition salt thereof, which compound is covalently coupled to a reporter group by the amino group, and antibodies prepared against a cannabinol metabolite conjugated at the 9 position to an immunogenic carrier, which antibodies are also capable of selectively binding the labeled compound;
   (b) separating the bound from the free labeled compound;
   (c) measuring the amount of either the free or the bound labeled compound;
   (d) comparing the amount of the labeled compound measured to values obtained from samples containing known amounts of a cannabinol metabolite; and
   (e) determining the amount of cannabinol metabolites in the sample from the comparison of step (d).

6. The method of claim 5 in which the antibodies are immobilized on a solid support.

7. The method of claim 5 in which the reporter group is an enzyme.

8. The method of claim 7 in which the enzyme is a peroxidase.

* * * * *